(12) United States Patent
von Falkenhausen

(10) Patent No.: US 6,414,264 B1
(45) Date of Patent: Jul. 2, 2002

(54) LASER BEAM CUTTING METHOD FOR CUTTING LAMINATES FOR APPLYING TO THE SKIN

(75) Inventor: Christian von Falkenhausen, Bonn (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

(21) Appl. No.: 09/530,376

(22) PCT Filed: Oct. 29, 1998

(86) PCT No.: PCT/EP98/06861
§ 371 (c)(1),
(2), (4) Date: Apr. 27, 2000

(87) PCT Pub. No.: WO99/24213
PCT Pub. Date: May 20, 1999

(30) Foreign Application Priority Data

Nov. 8, 1997 (DE) .......................................... 197 49 525

(51) Int. Cl.[7] .............................................. B23K 26/04
(52) U.S. Cl. ............................ 219/121.72; 219/121.44; 219/121.58; 83/373
(58) Field of Search .......................... 219/121.72, 121.7, 219/121.69, 121.68, 121.67, 121.71, 121.39, 121.58, 121.59, 121.82; 83/373

(56) References Cited

U.S. PATENT DOCUMENTS

| | | | |
|---|---|---|---|
| 3,226,527 A | * | 12/1965 | Harding |
| 3,614,369 A | * | 10/1971 | Medley |
| 4,639,572 A | | 1/1987 | Gruzman et al. ..... 219/121 LG |
| 4,672,168 A | * | 6/1987 | Saunders et al. |
| 4,680,442 A | * | 7/1987 | Bauer et al. |
| 4,740,668 A | * | 4/1988 | Perez |
| 4,867,150 A | * | 9/1989 | Gilbert |
| 5,013,275 A | * | 5/1991 | Kautz |
| 5,135,156 A | * | 8/1992 | Bower |
| 6,090,330 A | * | 7/2000 | Gawa et al. |
| RE37,237 E | * | 6/2001 | Lancaster, III et al. |

FOREIGN PATENT DOCUMENTS

| | | |
|---|---|---|
| EP | 0 418 607 A | 3/1991 |
| EP | 0 738 556 A | 10/1996 |
| FR | 2 740 714 A | 5/1997 |
| WO | 41 10 027 A | 10/1992 |
| WO | WO 95/17304 A | 6/1995 |
| WO | WO 97 11841 A | 4/1997 |

OTHER PUBLICATIONS

Heilmann K., "Konzept und DeRealisaton programmierter Arzneiverabreichung" *Therapeutische Systeme* 1984 4:27–37.

* cited by examiner

*Primary Examiner*—M. Alexandra Elve
*Assistant Examiner*—Jonathan Johnson
(74) *Attorney, Agent, or Firm*—Jordan and Hamburg LLP

(57) ABSTRACT

The invention relates to a process for cutting laminates intended for application to the skin, including the following steps. (1) a laminate having at least one film and at least one further layer is supplied, (2) the laminate is transported to a cutting area of a laser beam cutting arrangement, whereby it is kept flat in the cutting area under a tension of between 0.1 N/m and $1 \times 10^4$ N/m by tightening the laminate synchronously in all four directions to the tightening plane, and (3) the laminate is cut into or cut through by laser beams.

16 Claims, 3 Drawing Sheets

LASER BEAM CUTTING METHOD FOR CUTTING LAMINATES FOR APPLYING TO THE SKIN

BACKGROUND OF THE INVENTION

The invention relates to a process for cutting laminates intended for application to the skin. These laminates include at least one film and at least one further layer and are suitable for the medicinal-pharmaceutical application to the skin.

The production of plasters from base material in the form of a web (laminate) is usually carried out, as, e.g., in DE-A 41 10 027, by mechanically punching into or punching through the laminate web. The punching knife hereby includes of a strip steel cutting tool which is, e.g., embedded and fixed in a wooden template. During the punching, the punching knife is driven onto the laminate web with a varying dynamic force according to the structure of the laminate, and punctures the laminate layers up to a determined punching depth. Ideally, the strip steel cutting tool is arranged exactly horizontally in relation to the laminate web, so that all points of the laminate along the strip steel cutting tool are punctured simultaneously and up to the same depth.

The constant repetition of these procedure steps, however, results in a deviation from the above mentioned ideal conditions in the production process which is more or less early and strong depending on the material. The reasons for this are the wear of the strip steel cutting tool on the one hand, but also the less than ideal fixing of the same in the template as well as other factors such as the not exactly horizontal lowering of the punching tool onto the laminate. This results in an increase of faulty punching processes, so that the laminate layers to be cut through are not completely severed. The following removal of the excess part of the laminate, i.e. the unchaining, is thus rendered considerably more difficult, resulting in increased material spoilage. A regular exchange of the strip steel cutting tools after certain intervals of time thus becomes necessary, which leads to increased costs as a result of the necessary machine preparation periods and starting losses. In addition, the punch dies themselves are subject to considerable wear and necessitate routine maintenance.

WO-A 95/17304 teaches a process for the cutting to size of labels which are applied to packages by means of laser beams.

WO-A 97/11841 describes a process for the production of self-adhesive labels. These self-adhesive labels are cut from a material in the form of a web by means of a cutting head using laser beams, whereby the material is held beneath the cutting head by an underpressure tightening device.

SUMMARY OF THE INVENTION

It is the object of the invention to provide a process for cutting laminates intended for application to the skin, the process having less tool wear and less material waste and being altogether less expensive than known processes of this kind through savings in machine preparation periods etc. The process should especially be highly variable, so that it is, e.g., no longer necessary to develop a separate punching press for every desired form of the laminate to be punched out.

This object is achieved by means of a process for cutting laminates intended for the skin comprising the following steps: a laminate comprising at least one film and at least one further layer is supplied, the laminate is transported to a cutting area of a laser beam cutting arrangement, whereby it is kept flat in the cutting area under a tension of between 0.1 N/m and $1 \times 10^4$ N/m, and it is cut into or cut through by means of laser beams.

In the process according to the invention, the tension to which the laminate intended for application to the skin is subjected is preferably at a value of between 600 and 3000 N/m, especially between 1000 and 2000 N/m. This tension can be adjusted by means of common devices located outside of the cutting area. Such devices used according to the invention can especially be conceived as tong-like pulling devices located in front of and/or behind the cutting area and operating in a fixed cycle, which, e.g., transport the material against the braking effect of a slipping clutch of the laminate supplying device or else have different pulling lengths, whereby the front pulling device, seen in direction of the laminate supply, has a slightly longer pulling length than the rear one.

According to a further aspect of the invention, a process for cutting the medicinal-pharmaceutical laminate is provided which includes the following steps: a laminate having at least one film and at least one further layer supplied, the laminate is transported to a cutting area of a laser beam cutting arrangement, whereby it is kept flat in the cutting area by means of a fixing device, and it is cut into or cut through by means of laser beams.

The two processes according to the two central aspects of the invention, as described above, can, of course, also be combined with one another.

The fixing devices can especially be conceived as a fixable framelike holding device optionally fastened on ball bearings, e.g., in the form of an "active tightening frame" (FIGS. 2A,B) described below, or as a holding device with perforations on the upper side, whereby the relative surface proportion of the perforations, in relation to the surface of the upper side of the fixing device which faces the laser beam, is greater than 50%. Preferably, this proportion is greater than 90%, especially greater than 99%. Preferably, the perforations have a honeycombed form.

Other preferred fixing devices are transparent covering devices, e.g., made of glass, plastics such as plexiglass etc., which have an absorbing band diverging from the laminate. Devices based on combinations of the above mentioned framelike holding device, the holding device with perforations or the transparent covering device are also applied according to the invention.

According to the invention, the laminate suited for application to the skin can be flooded with inert gas during the cutting process. Using certain materials, undesired oxidation processes during cutting can thus be avoided. In addition, by supplying inert gas during cutting, vaporizing material can be blown away or sucked off, whereby impairments of the laminate surface are avoided. Such impairments can, e.g., consist in that vaporized or otherwise dissolved particles connect with the laminate surface and impair its characteristics in an undesired way. In this context, the term "vaporize" used above is to be interpreted in a broad sense. It is not only to be understood to mean that a solid material passes over into the vapor phase during the laser cutting process; rather, it also includes particles present in solid phase having a size in the realm of mm or even mm or smaller (described in the following as micro- or nanoparticles). In the following, the inert gas used according to the invention is understood to be a gas such as nitrogen, argon or helium, etc. The supply and flooding with inert gas during cutting can especially be used to support the flat resting of the laminate on the fixing device. This can, e.g., occur by means of overpressure. The gas can be supplied parallel to the laser beam and then, e.g., be sucked off my means of underpressure. For this, the holding device with perforations according to the invention can be used. On the other hand, the gas can also be supplied from the side, e.g., by means of nozzles located above and parallel to the laminate.

Of course the flat resting of the laminate can also be supported by applying underpressure to the laminate underneath the cutting area, for which the above mentioned device with perforations is especially suited. If the laminate is laid on this device for cutting, the laminate can be held flat by applying underpressure to the laminate through the perforations underneath.

The laminates for application to the skin used according to the invention are basically to be understood as all single or multilayered laminates whose materials are so constituted that they are suitable for longer-term wearing on the skin. This not only includes the known "tapes" such as Hansaplast® g, Leukosilk®, Leukoplastg® etc., but also common plaster materials, especially active substance-containing plasters such as transdermal therapeutic systems (TTS). Such transdermal therapeutic systems are described in K. Heilmann, "Therapeutische Systeme Konzept und Realisation programmierter Arzneiverabreichung" (4th edition, 1984). Such TTS generally include a backing layer, a single or multilayered reservoir or matrix, and an optionally removable protective layer in the form of a film. The backing layer can be made of flexible or non-flexible material. Substances used for its production are polymeric substances such as polyethylene, polypropylene, polyethylene terephthalate, polyurethane, or polyamide. Other possible materials are polyvinyl alcohol, styrene-diene block copolymers, polyvinyl chloride, polymethacrylate, to name only several more examples. Of course combinations of the above mentioned materials can also be used. As further materials, films damped with metal, e.g., film damped with aluminum, are also used alone or coated with a polymer substrate. Textile sheet materials are also used, at least as long as they cannot be penetrated by the components of the reservoir or matrix.

Basically, the same materials can be used for the removable protective film, the film must, however, additionally be adhesively equipped. This adhesive equipment can be achieved through a special siliconizing process. The reservoir or matrix, which can, as mentioned above, include one or more layers, generally contain one or more active substances as well as additional auxiliary substances as additives and a polymer material. Possible polymers are, e.g., polyisobutylene, esters of polyvinyl alcohol, esters of polyacrylic acid and polymethacrylic acid, natural rubber, styrene, isoprene and styrene-butadiene polymerizates, silicon polymers, resin components such as saturated or unsaturated hydrocarbon resins, derivates of abiethyl alcohol and β-pinene, plasticizers such as phthalic acid esters, triglyderides and fatty acids. The polymer material of the matrix can also be based on polymers such as rubber, rubberlike synthetic homo-, co- or block polymers, polyurethanes, copolymers of ethylene, or polysiloxanes.

The mentioned additives, also referred to as auxiliary substances, are divided into plasticizers, tackifiers, resorption improvers, stabilizers or filling materials according to their function. Such materials, which must be physiologically harmless, are generally known to the person skilled in the art. For the laminates used in the process according to the invention, especially for the laminates from which TTS are produced, basically all pharmaceutical active agents suited for dermal application can be used. Suitable active agents are found in the active agent groups of parasympatholytics (e.g., scopolamine, atropine, benactyzine) cholinergics (e.g., physostigmine, nicotine), neuroleptics (e.g., chlorpromazine, haloperidol), monoamino oxidase inhibitors (e.g., tranylcypromine, selegiline), sympathomimetics (e.g., ephedrine, d-norpseudoephedrine, salbutamol, fenfluramine), sympatholytics and antisympathotonics (e.g., propanolol, timolol, bupranolol, clonidin, dihydroergotamine, naphazoline), anxiolytics (e.g., diazepam, triazolam), local anesthetics (e.g., lidocaine), central analgesics (e.g., fentanyle, sufentanil), antirheumatic agents (e.g., indomethacin, piroxicam, lomoxicam), coronary therapeutic agents (e.g., glycerol trinitrate, isosorbide dinitrate), estrogens, progestogens and androgens, antihistamines (e.g., diphenhydramine, clemastin, terfenadine), prostate glandin derivates, vitamins (e.g., vitamin E, cholecalciferol) and cytostatic agents.

The laminate can be conveyed to the cutting area either continuously or at intervals, whereby the moving speed of the laminate is controlled, preferably supported by a computer. All other procedure parameters of the laser cutting process for laminates according to the invention, such as laser performance, cutting speed etc. are, of course, also regulated with the support of a computer. In addition, the laser cutting process can, according to its nature, be both continuous and pulsed.

Therein, the laser beam moves over the laminate especially by means of controllable movable mirrors, prisms and/or beam dividers. Especially, a device is used for this which carries the laser beam-emitting apparatus and which is movable in two directions (x, y coordinates) through plotter guidance. As far as the laser itself is concerned, all common lasers can be used, e.g., excimer lasers (F2, ArF, KrF, XeCl, CO, CO2), gas lasers (Ar, HeNe), solid body lasers, and semiconductor lasers. The laser beam itself is preferably focused on the laminate by means of a lens system.

In the case of continuous laminate supply, the supply speed and/or laser movement are regulated according to the invention so that the chosen cut form is independent of the conveying speed. The cutting depth of the laser beam can be adjusted to be constant or variable. In this way, a kind of "perforation" can be achieved. In addition, however, in the process according to the invention the cutting depth of the laser beam, i.e. how deeply the supplied laminate should be cut into, can be so determined that the laminate is always cut into up to a certain depth regardless of possibly existing fluctuations in the thickness of the laminate. Accordingly, the cutting depth into a multilayered laminate can thus differ along the cutting direction. Even if the thickness of the laminate itself is not constant, but rather has more and less elevated areas alternating with one another, as can be the case with TTS, it can thus be achieved that the laminate is always cut into up to the same depth along the entire cut line. In this way, the thickness of the remaining rest of the laminate which is not cut into remains constant.

Especially, in the laser cutting process according to the invention the intensity distribution profile of the laser beam can also especially be adjusted or modulated. Thus, the thermal load of the workpiece can be controlled and so its characteristics can be influenced. The use of an intensity profile which slightly drops off at the sides, for example, can lead to the advantage that in the peripheral areas along the cutting edge, thermally determined changes of the material to be processed can be deliberately induced. Thus, the viscosity of the material in the area to be cut, e.g., can be purposely influenced. In the case of a simple cutting (through), on the other hand, the material stress along the cutting edge can be minimalized by a modulation of the intensity profile. This is achieved by using a very sharp-edged intensity profile. The intensity distribution profile of the laser beam necessary for achieving such cutting edge characteristics, however, also depends on the used laminate material and cannot be generally determined from the outset. For a certain determined laminate to be used, however, the person skilled in the art can determine the necessary intensity distribution of the laser beam necessary for achieving certain cutting edge characteristics by means of routine experiments.

BRIEF DESCRIPTION OF THE DRAWINGS

The process according to the invention is described in greater detail in the following figures and examples. The figures show the following.

DETAILED DESCRIPTION OF THE INVENTION

Figure 1A:
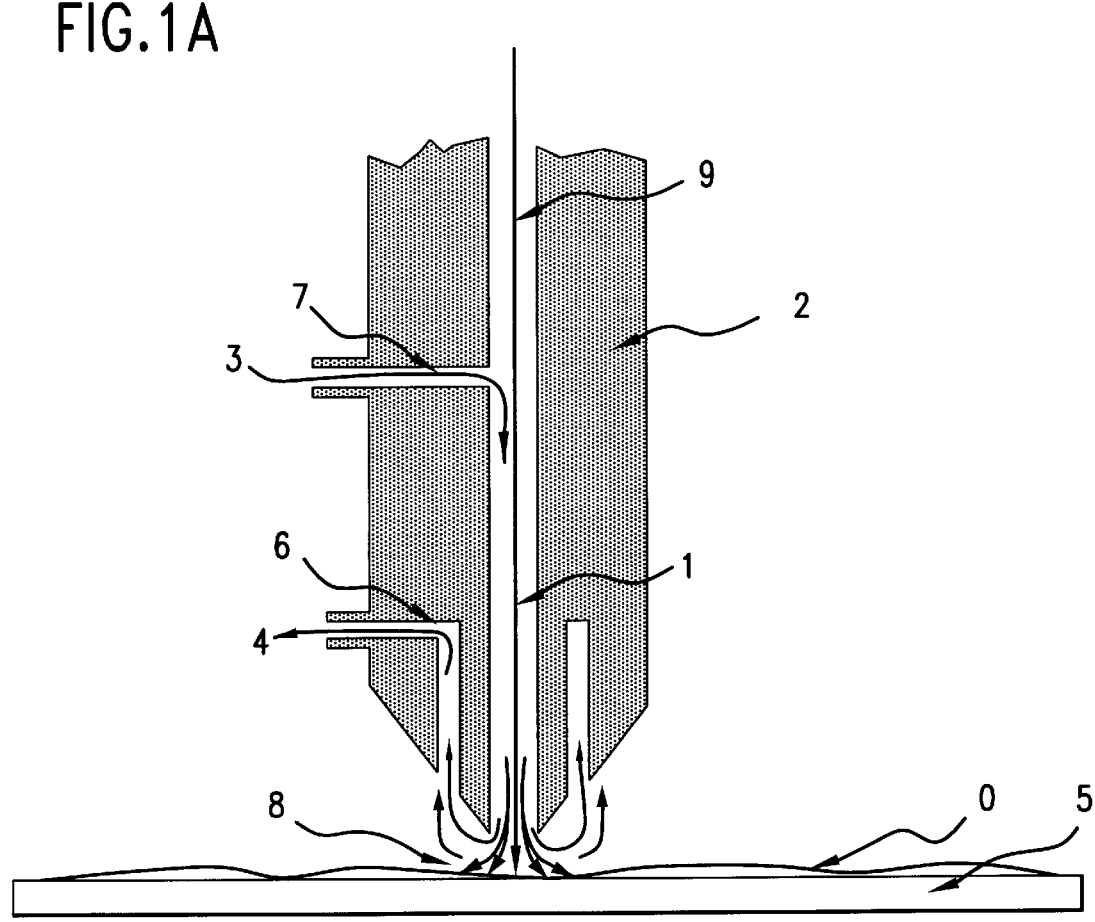
FIG. 1A is a side view of a device for aligning laminates.
Figure 1B:
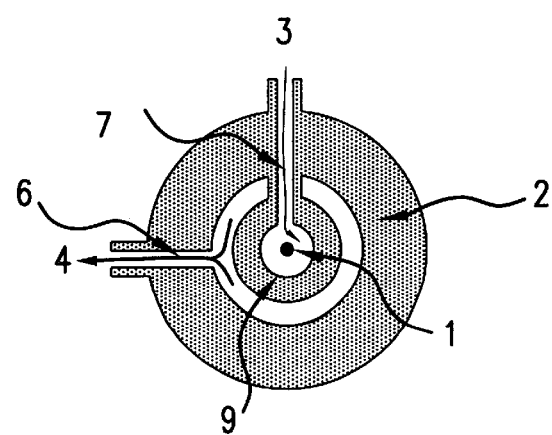
FIG. 1B is a top view of a device for aligning laminates.

FIG. 1 shows a device used according to the invention which aligns the laminate 0 flatly on the carrier 5 in the vicinity of the cutting zone 8 by means of overpressure. This is achieved through a special cutting head 2 (FIG. 1A, side view; FIG. 1B, top view/cross-sectional view) which is guided over the laminate. The cutting head includes a central channel 9 through which the laser beam 1 is guided. This channel can be flooded either with air or a special process gas 3 through a lateral inlet/outlet opening 7. The gas streams onto the laminate 0 to be cut under increased pressure and presses the laminate against a carrier 5 in the vicinity of the cutting area 8. The laminate is thus flatly fixed in this area. A further channel 6, which circularly surrounds the central channel 9 and has a separate inlet/outlet opening, enables the drawing off, if necessary, of particle vapor or gases 4 formed during the cutting process. The openings 6 and 7 can optionally be used as inlet openings and/or outlet openings. Thus, in a special embodiment of the device, a further process gas can be supplied through the opening 6. Furthermore, the opening 7 can be used as a suction channel.

Figure 2A:
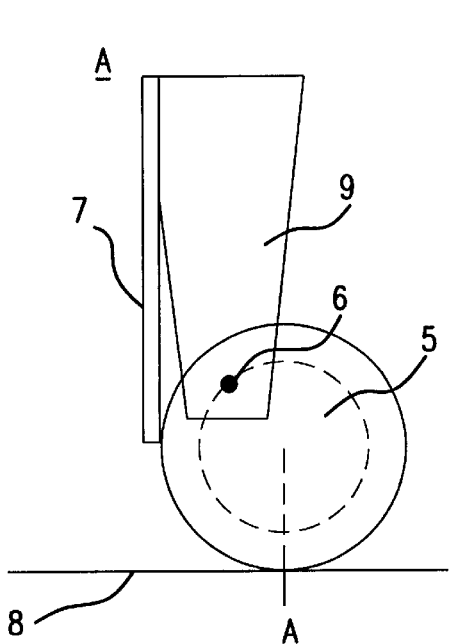
FIG. 2A is a cross section of a fixing device.
Figure 2B:
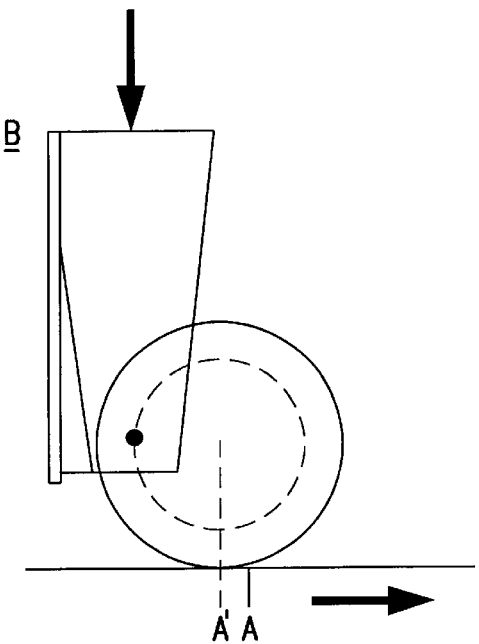
FIG. 2B is a cross section of a fixing device.
Figure 2C:
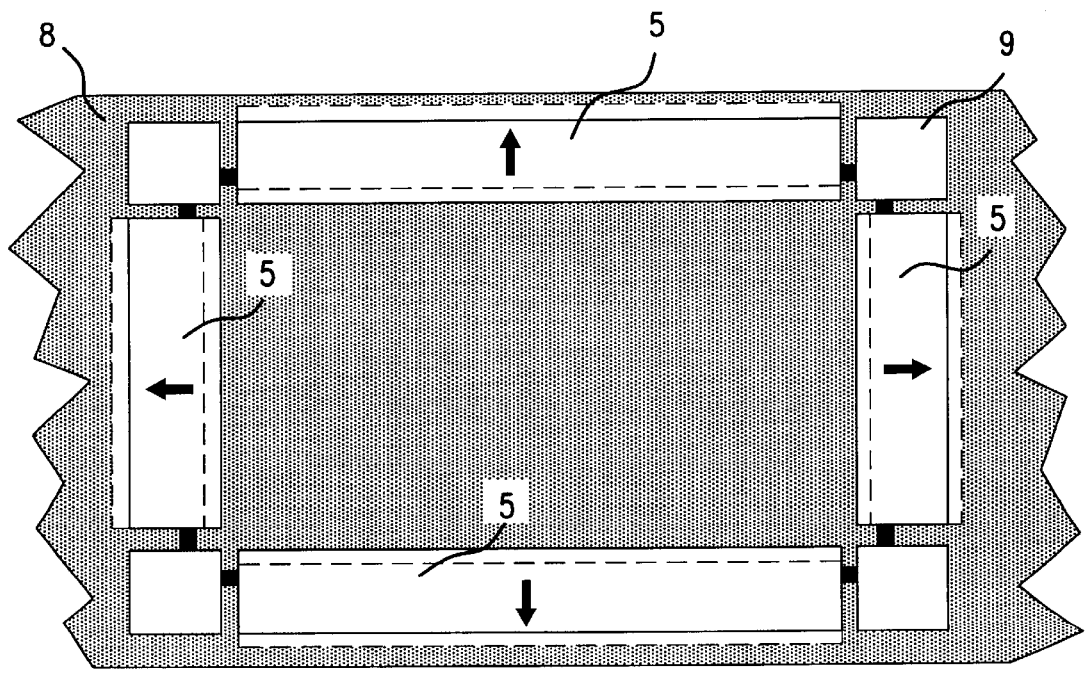
FIG. 2C is a top view of the fixing device.

FIG. 2 shows the cross-section of the fixing device according to the invention in the form of an active tightening frame on ball bearings in a side view (upper drawing, FIGS. 2A, 2B) and in top view (lower drawing, FIG. 2C). The tightening frame has two pairs of eccentrically fixed rolls 5, the pairs arranged at a right angle to one another, whereby the rolls of one pair are positioned parallel to one another. The pivots 9 of the rolls form a rectangular frame; at its narrowest point at right angles to the laminate 8, the perforation of the frame releases at least 80% of the width of the laminate. If the laminate 8 is fixed or tightened in the laminate plane, the lowering of the frame, i.e. of the rolls 5, results in that the laminate 8 is transported from the point of support A or A' (FIG. 2 A,B) in the direction of Point B (FIG. 2B) due to the eccentric bearing 6 of the rolls 5. As this occurs synchronously in all four directions of the tightening plane, it results in a fixing of the laminate. In a state of rest of the rolls 5 of the holding frame, the stopper 7 prevents the hanging down of the rolls and thus secures the direction of the conveying process when the rolls are lowered. Another embodiment (not shown) of the active tightening frame solely includes a pair of tightener rolls arranged parallel to one another, so that the material is only tightened in direction of the laminate transport or at right angles thereto.

Figure 3:
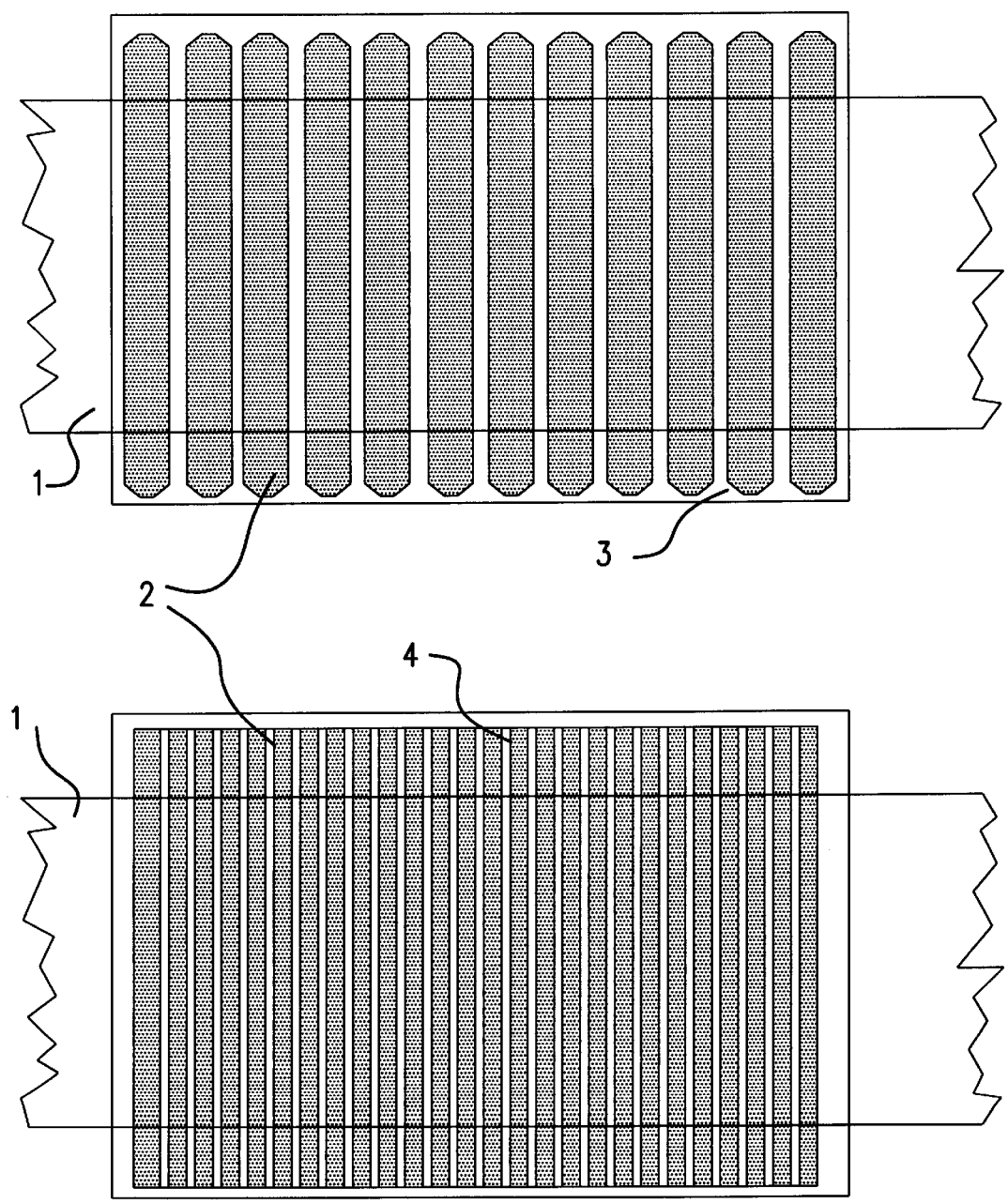
FIG. 3 is a top view of the fixing device.

FIG. 3 shows a top view of an embodiment of the fixing device with perforations, the embodiment being in the form of a vacuum table 3. The shown fixing device is so embodied that it is especially suited for cutting through the laminate 1. The perforations 2, which are recognizable as ovals in the top view, have a cross-sectional width at their narrowest point corresponding to at least the triple value of the diameter of the laser beam. Preferably, the width of the perforations is between 3 and 100 times the value of the diameter of the laser beam. The total proportion of the perforations of the surface of the upper side across from the laser beam is greater than 90%; in the shown especially preferred embodiment, in which the perforations are only separated from one another through narrow cross-pieces 4 of, e.g., metals such as aluminum, it is greater than 99%.

What is claimed is:

1. A process for cutting laminates for application to skin, comprising:

providing a laminate comprising at least one film and at least one further layer;

transporting said laminate to a tightening plane in a cutting area of a laser beam device;

keeping said laminate flat in the cutting area under a tension of between 0.1 N/m and $1 \times 10^4$ N/m by tightening said laminate synchronously in all four directions of the tightening plane; and cutting into or through said laminates while under said tension using said laser.

2. The process for cutting laminates according to claim 1, wherein said laminate is kept flat in the cutting area of a laser beam under tension in all four directions of the tightening plane using a fixing device.

3. The process of claim 2, wherein the fixing device is a holding device having a frame which has two pairs of excentrically fixed rolls, the pairs of the rolls are arranged at a right angle to one another, and the rolls of one pair are positioned parallel to one another.

4. The process of claim 3, wherein the fixing device includes a holding device with perforations in an upper side thereof and a relative surface proportion of the perforations in relation to a surface area of the upper side is greater than 50%.

5. The process of claim 3 wherein the fixing device includes a transparent cover device.

6. The process of claim 1 wherein inert gas is supplied during cutting.

7. The process of claim 4 wherein one of over pressure and under pressure is applied to support the flattening of the laminate.

8. The process of claim 4 wherein the relative surface proportion of the perforations in relation to the surface area of the upper side is greater than 90%.

9. The process according to claim 4 wherein the perforations have a cross-sectional diameter at a narrowest point corresponding to at least triple a value of a diameter of the laser beam.

10. The process of claim 2 wherein the fixing device includes a thermally resistant material.

11. The process of claim 10 wherein the thermally resistant material is one of aluminum, asbestos, kevlar, glass, metals and alloys, and plastics.

12. The process of claim 1 wherein said laminate is supplied continuously and a supply speed and a movement of the laser beam cutting device are regulated so that a chosen cut form is independent of a relative speed of the laminate to the laser beam.

13. The process of claim 1 wherein a thickness of the laminate is measured and procedure parameters are regulated so that a cutting depth occurs up to a determined layer of the laminate.

14. The process of claim 1 wherein the laminate is cut into with a variable cutting depth varied by means of regulation of the laser beam and a relative speed of the laminate to the laser beam.

15. The process of claim 1 wherein material vaporizing during the cutting process is removed.

16. The process of claim 1 wherein at least one of the further layers contains at least one active substance.

* * * * *